United States Patent [19]
Nagasaki

[11] Patent Number: 4,484,476
[45] Date of Patent: Nov. 27, 1984

[54] ACOUSTIC MICROSCOPE DEVICE

[75] Inventor: Tatsuo Nagasaki, Musashino, Japan

[73] Assignee: Olympus Optical Co., Ltd., Japan

[21] Appl. No.: 440,431

[22] Filed: Nov. 9, 1982

[30] Foreign Application Priority Data

Nov. 12, 1981 [JP] Japan .................................. 56-180297

[51] Int. Cl.³ ........................................... G01N 29/04
[52] U.S. Cl. ..................................................... 73/606
[58] Field of Search ................. 73/606, 626, 643, 644, 73/628; 310/313 B, 313 R

[56] References Cited

U.S. PATENT DOCUMENTS

| | | | |
|---|---|---|---|
| 3,647,899 | 10/1972 | Dias | 310/313 B |
| 3,845,420 | 10/1974 | Holland et al. | 310/313 B |
| 4,364,017 | 12/1982 | Tokunaga et al. | 310/313 R |

OTHER PUBLICATIONS

Weglein et al., "Scanning Acoustic Microscopy-Application to Fault Detection", 15th Annual Proceedings Reliability Physics, Las Vegas, Nev., USA, Apr. 12-14, 1977.

*Primary Examiner*—Anthony V. Ciarlante
*Attorney, Agent, or Firm*—Parkhurst & Oliff

[57] ABSTRACT

In an acoustic microscope device using an acoustic surface wave, a plurality of interdigital electrodes are provided on an acoustic surface wave propagating medium in a linear or circular manner, and these electrodes are selectively connected to a transmitting signal source via a multiplexer and respective delay lines having such delay times that the acoustic surface waves generated from the selected electrodes are focused at a focal point on the medium. The selection of the electrodes and the delay times of the delay lines are so changed that the focal point is moved two-dimensionally over the medium surface. The acoustic surface waves reflected at the focal points are received by the selected electrodes and electric signals from the electrodes are summed through the delay lines to derive an image signal at the relevant focal point. In this manner, a tomographic image of a specimen near its surface which is made in contact with the medium is formed.

9 Claims, 12 Drawing Figures

FIG_2A
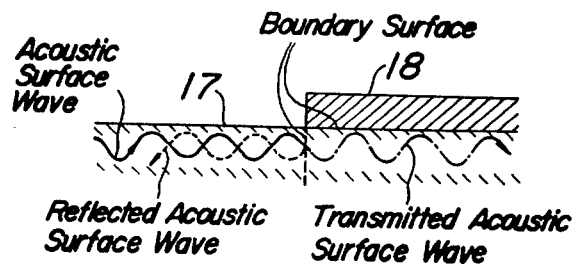
FIG_2B
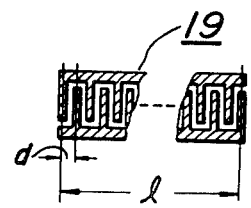
FIG_2C
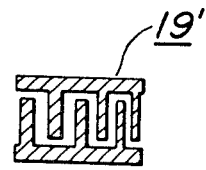

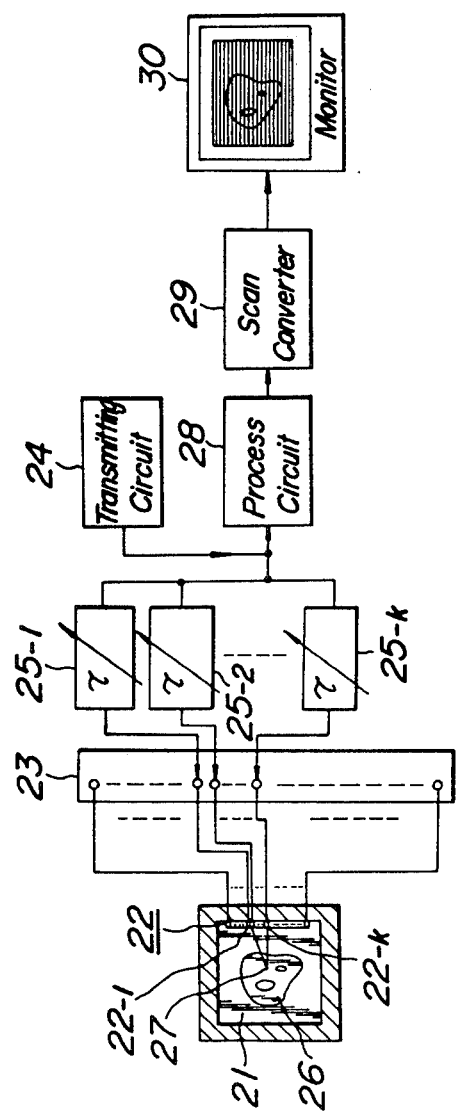

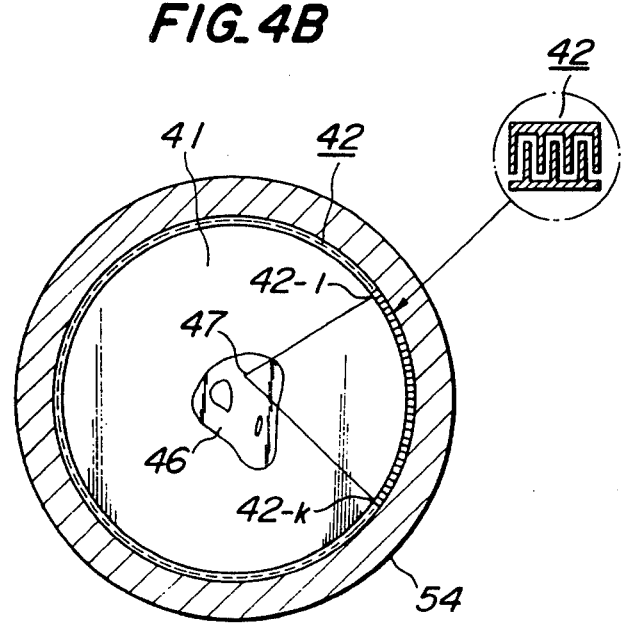
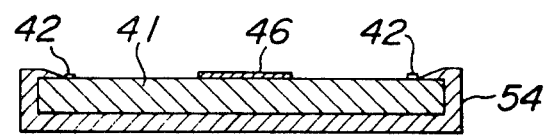

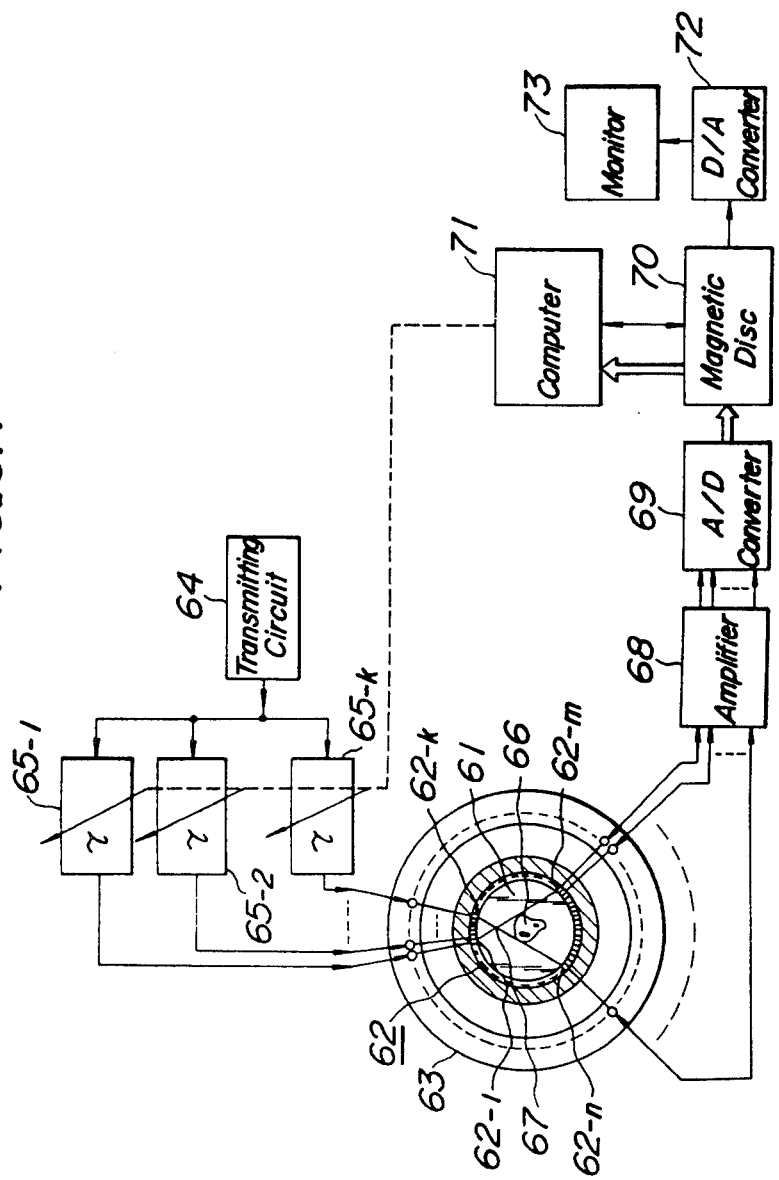

ACOUSTIC MICROSCOPE DEVICE

BACKGROUND OF THE INVENTION

The present invention relates to an acoustic microscope device using an acoustic surface wave.

FIG. 1 shows a construction of a known acoustic microscope device. A gate signal generated by a gate signal generator 1 is supplied to a transmitting circuit 2 to gate transmitting output signals. Several tens waves thus gated are supplied via a circulator 3 to a matching box 4 in which an impedance matching is effected. The transmitting signals are further supplied to a vibrating element 5 made of piezoelectric material to produce an acoustic wave. The acoustic wave transmitted by the element 5 is focused by an acoustic lens 6 via an acoustic wave propagating medium 7 such as water onto a specimen 8. The acoustic wave reflected by the specimen 8 is collected by the acoustic lens 6 and received by the vibrating element 5 to produce a reflection signal. The reflection signal produced by the vibrating element 5 is supplied through the matching box 4 and circulator 3 to a receiving gate circuit 9 to which is also supplied the gate signal from the gate signal generator 1. The receiving gate circuit 9 selects only the reflection signal and the selected reflection signal is amplified and detected by a receiving amplifier 10. The output signal from the amplifier 10 is further peak-detected by a video process circuit 11. A specimen 8 is placed on a specimen holder 13 which is driven two-dimensionally by a mechanical scanner 12. Therefore, it is possible to obtain a two-dimensional distribution signal of the peak values of the reflection signal supplied from the video process circuit 11. This signal is converted into a television signal by means of a scan converter 14 and the television signal thus converted is displayed on a television monitor 15. The gate signal generator 1 and video process circuit 11 are synchronously driven by a clock generator 16.

In the known acoustic microscope device mentioned above, in order to increase a resolution of the displayed image it is necessary to increase the frequency of the acoustic wave. However, if the frequency is increased, the acoustic wave is decayed in proportion to a square of the frequency. For instance, the acoustic longitudinal wave of 500 MHz is absorbed in water of 20° C. by 50 dB/mm, the water being usually used as the propagating medium 7. Therefore, the resolution of the known acoustic microscope device is limited. Further, the resolution may be increased by increasing a curvature of the acoustic lens 6. However, the curvature of the lens 6 could not be made large enough due to the fact that the lens might be close to the specimen 8 to an inadmissible extent.

The known acoustic microscope device has another drawback that the scanner 12 for scanning the specimen 8 mechanically is liable to be large in size and complicated in construction.

SUMMARY OF THE INVENTION

The present invention has for its object to provide a novel and useful acoustic microscope device having a high resolution by utilizing an acoustic surface wave.

It is another object of the invention to provide an acoustic microscope device which can be made small in size and simple in construction.

According to the invention, an acoustic microscope device for producing an image of a specimen to be inspected comprises an acoustic surface wave propagating medium which is to be made in contact with the specimen;

a plurality of electrodes arranged on said medium with a given pitch for generating an acoustic surface wave along a surface of the medium; and circuit means connected to said electrodes for selectively connecting at least a part of the electrodes into a circuit; whereby the acoustic surface waves are radiated from the selected electrodes along the surface of the medium to scan the specimen and the acoustic surface waves modulated in accordance with a difference in acoustic impedance between the specimen and the medium are received so that image information about the specimen being in contact with the medium is obtainable.

BRIEF DESCRIPTION OF THE DRAWINGS

FIGS. 2A, 2B and 2C are schematic views for explaining a principle of the present invention and illustrating a construction of an acoustic surface wave electrode;

FIGS. 3A, 3B and 3C are schematic views depicting a first embodiment of the acoustic microscope device according to the invention;

FIGS. 4A, 4B and 4C are schematic views illustrating a second embodiment of the acoustic microscope device according to the invention; and FIGS. 5A and 5B are schematic views showing a third embodiment of the acoustic microscope device according to the invention.

DESCRIPTION OF THE PREFERRED EMBODIMENTS

Figure 1:
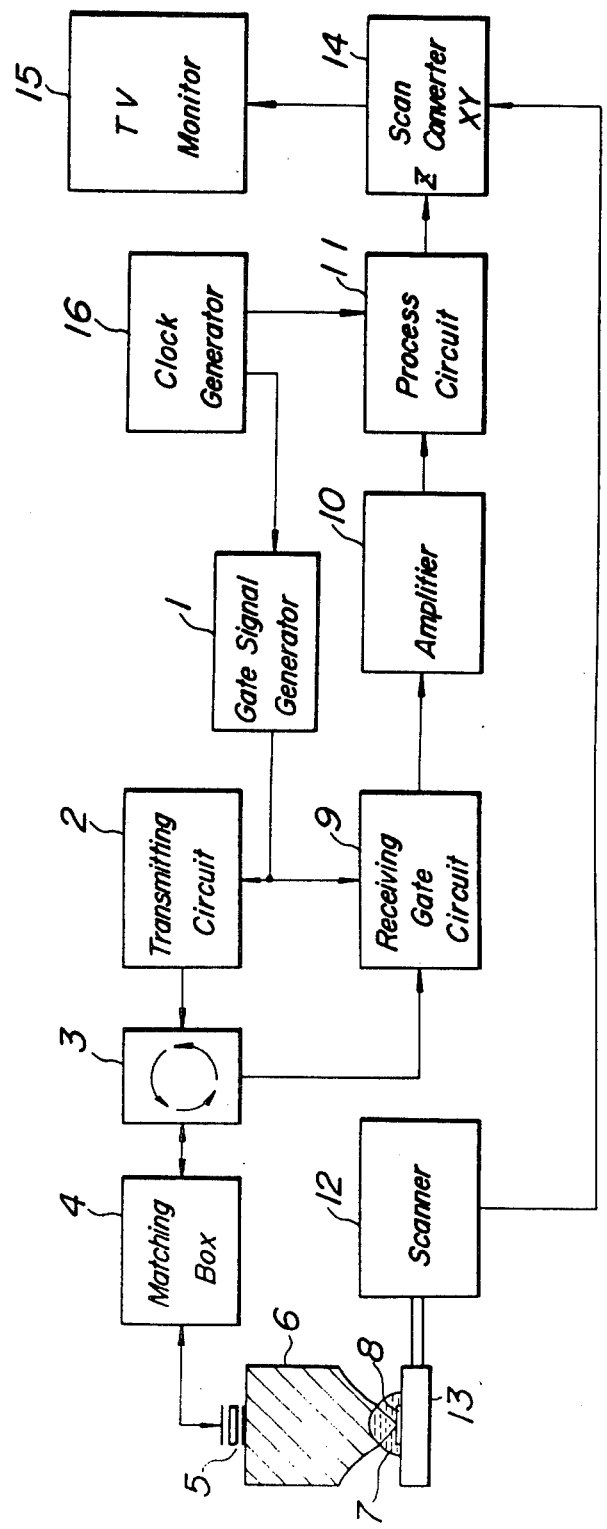
FIG. 1 is a schematic view showing a known acoustic microscope device.

At first, the principle of the present invention will be explained with reference to FIG. 2A. In FIG. 2A, an acoustic surface wave propagating medium 17 is made in contact with a specimen 18 and an acoustic surface wave propagating along a surface of the medium 17 is reflected by a boundary surface between the medium 17 and the specimen 18 due to a difference in acoustic impedance therebetween. An amount of the reflected acoustic surface wave is proportional to the difference. The acoustic surface wave is further decayed, while it propagates under the specimen. An amount of the absorbed acoustic energy is inversely proportional to said difference. The present invention utilizes such a phenomenon to obtain a two-dimensional distribution of the acoustic impedance over the boundary surface between the medium 17 and the specimen 18. In case of utilizing the reflected acoustic surface wave, an image of the specimen 18 can be obtained in a similar manner to the radar and the ordinary acoustic diagnosis device, while in case of using the transmitted acoustic surface wave, an image can be displayed in a similar manner as the computed tomography. Since the acoustic surface wave has a very low velocity in comparison with longitudinal and transverse waves and has a shorter wavelength, it is possible to attain the high resolution. For example, the velocity of the longitudinal wave used in the known acoustic microscope in the water is 1,530 m/sec, whereas the acoustic surface wave in the propagating medium 17 made of polyethylene is 490 m/sec.

FIG. 2B is a plan view showing an electrode 19 of interdigital form for generating the acoustic surface wave. The electrode 19 is provided on a piezo-electric member serving also as the acoustic surface wave propagating medium. A wavelength $\lambda$ of the acoustic surface wave is determined by a pitch d of the electrode 19 and is expressed by $\lambda=2d$ and a frequency range B is proportional to a length l of the electrodes. In this manner, a high frequency up to several giga hertz can be used and thus a very high resolution can be attained. In case of displaying the image on the basis of the reflection method, use may be made of an electrode 19' having a decreasing pitch as illustrated in FIG. 2C, which is similar to matching electrodes for use in the pulse compression. Therefore, the known pulse compression technique (frequency composition technique) can be utilized as it is, so that the range resolution can be further increased. Moreover, the propagation of the acoustic surface wave is considered to be a two-dimensional space frequency and therefore, use may be made of an aperture composing technique based on the mapping radar (side looking radar) principle and an azimuth resolution can be increased materially.

In case of using the transmitted acoustic surface wave to obtain the image in the similar principle as the computed tomography, the resolution can be principally increased to a desired extent by increasing a magnitude of a reproduced area and the number of parameters, although a time required for obtaining a completed image is prolonged.

Figure 3B:
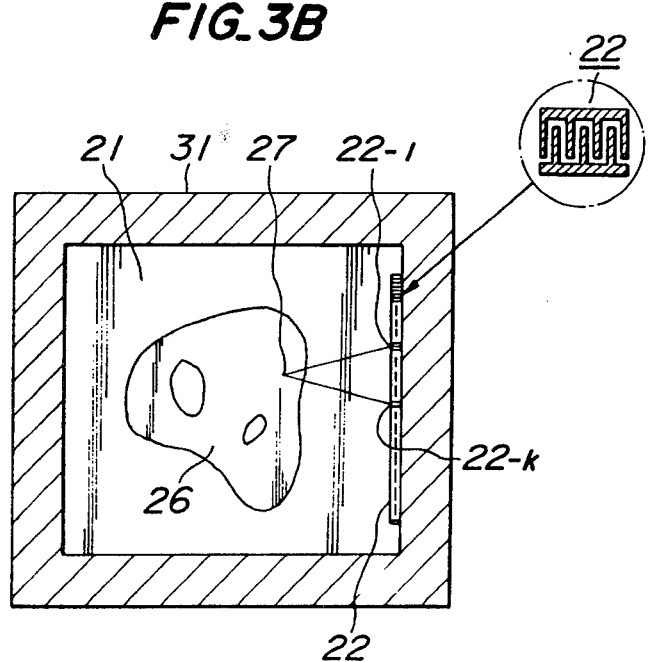
Figure 3C:
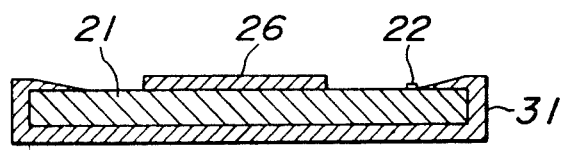

FIG. 3A is a schematic view showing a whole construction of a first embodiment of the acoustic microscope device according to the invention. In this embodiment, a series of acoustic surface wave wide range electrodes 22 is provided on a piezo-electric body 21 as shown in FIGS. 3B and 3C. A group of electrodes 22-1 to 22-k are selected by a multiplexer 23 and a transmitting pulse from a transmitting circuit 24 is supplied through respective delay lines or phase shifters 25-1 to 25-k to respective electrodes in such a manner that the transmitted acoustic surface wave pulses are focused at a point 27 on a specimen 26 to be sampled. That is to say, the delay lines 25-1 and 25-k have such delay times that the acoustic surface wave pulses generated by the electrodes 22-1 to 22-k are concentrated at the point 27 to be inspected.

The acoustic surface wave pulses reflected by the specimen 26 at the point 27 are received by the electrodes 22-1 to 22-k from which the acoustic surface wave pulses have been transmitted and are converted into reflection signals. These reflection signals are delayed by the delay lines 25-1 to 25-k and then are summed. By this measure, a so called focus-on reception can be effected. By changing the delay amounts in the delay lines 25-1 to 25-k and the number of the electrodes to be selected by the multiplexer 23, it is possible to move the focal point 27 in a direction perpendicular to the electrode array, while the focusing degree is maintained same. Further, by moving the position of the electrodes to be selected by the multiplexer 23, the focal position 27 can be moved on the specimen 26 to effect a two-dimensional scan. The deflection signal obtained at respective focal points is amplified and detected in a process circuit 28. In this circuit 28, only the reflection signal from the focal point is sampled and held and then is further corrected for a decay due to a distance by means of a time gain control. The deflection signal thus processed is converted into a television signal by a scan converter 29 and the converted signal is displayed on a television monitor 30. As best shown in FIGS. 3B and 3C, the piezo-electric body 21 is surrounded by a frame member 31 made of acoustic surface wave absorbing material having an acoustic impedance same as the piezo-electric body 21. In the present embodiment, since the piezo-electric body 21 can be made very small, it can be easily installed in an endoscope to obtain a gastroscope, hysteroscope, various kinds of operating scopes, etc.

Figure 4A:
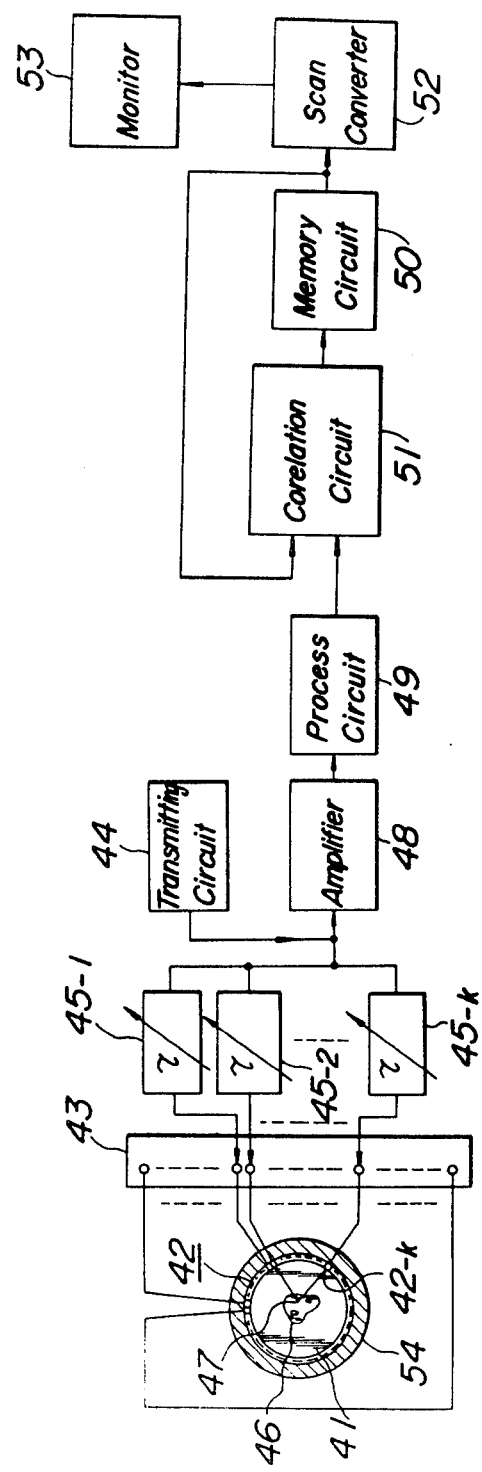

FIGS. 4A, 4B and 4C show a second embodiment of the acoustic microscope device according to the invention. In this embodiment, on a disc shaped piezo-electric body 41 are arranged acoustic surface wave wide range electrodes 42 in a ring-shaped manner. Among these electrodes, k electrodes 42-1 to 42-k are selected by means of a multiplexer 43 and a transmitting pulse generated from a transmitting circuit 44 is supplied via delay lines or phase shifters 45-1 to 45-k to the electrodes 42-1 to 42-k to generate acoustic surface wave pulses. The delay times of the delay lines 45-1 to 45-k are so chosen that the acoustic surface wave pulses are focused at a point 47 on a specimen 46. The acoustic surface wave pulses reflected by the specimen 46 at the point 47 are received by the electrodes 45-1 to 45-k from which the acoustic surface wave pulses have been generated to produce reflection signals. The reflection signals are delayed by the delay lines 45-1 to 45-k and then are summed. The summed signal is amplified and detected by an amplifier 48 and is further sampled and held by a process circuit 49 in which the decay of the wave with respect to the distance is compensated for to effect the time gain control. The deflection signal thus processed is stored in a memory circuit 50.

The position of the electrodes selected by the multiplexer 43 is changed successively one by one such as 42-2 to 42-(k+1); 42-3 to 42-(k+2); and so on. During this operation, the delay times of the delay lines 45-1 to 45-k are so changed that the acoustic surface wave pulses are always focused at the same point 47. This may be effected by means of any one of known measures such as a computer. Then, the reflection signal is compared with that previously stored in the memory circuit 50 in a correlation circuit 51 and a summation average, product average, etc. are produced. The average signal thus derived is stored again in the memory circuit 50. The above operation is repeated, while the position of the electrodes is successively shifted. After the electrodes 42 have been driven by one turn, the point 47 to be sampled is successively shifted two-dimensionally by an amount equal to a half of the resolution by changing the delay times of the delay lines 45-1 to 45-k. The sampled signals thus derived successively are converted by a scan converter 52 into a television signal which is then supplied to a television monitor 53. Also in this embodiment, the piezo-electric body 41 is surrounded by an acoustic surface wave absorbing member 54 for avoiding undesired reflection.

In the second embodiment, although the system is complicated and the time required for obtaining the complete image is long, it is possible to obtain an image having extremely high resolution and quality as compared with the first embodiment, because the side lobes and superimposition are effectively removed. Further, since the image quality may be improved by an electrical treatments corresponding to a matched filter, the resolution may be further improved.

Figure 5B:
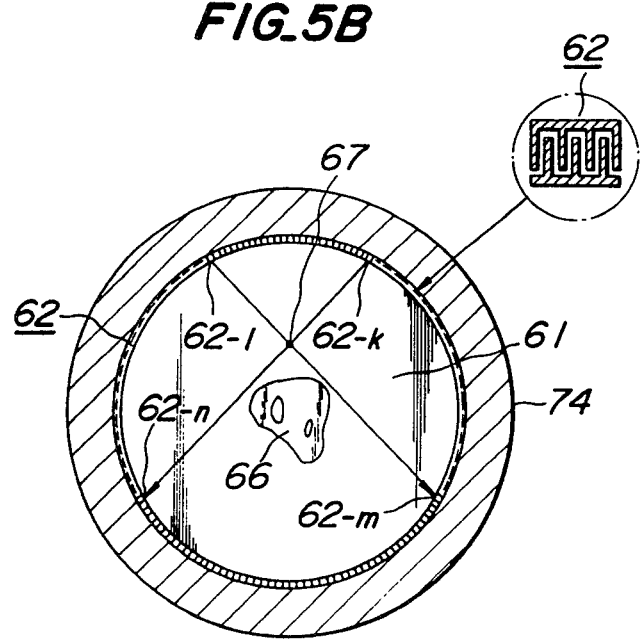

FIGS. 5A and 5B illustrate a third embodiment of the acoustic microscope device according to the invention. In the present embodiment, the acoustic surface wave transmitted through the specimen is received and an image is displayed on the basis of the principle similar to the computed tomography. The propagation of the acoustic surface wave may be recognized to be a two-dimensional space frequency and a resolution in a direction perpendicular to the surface of the piezo-electric body is not necessary to be considered. Therefore, the algorism for the computed tomography can be applied as it is. In this embodiment, acoustic surface wave wide range electrodes 62 are provided on a disc-shaped piezo-electric body 61 in a ring-shape with a given pitch. A group of electrodes 62-1 to 62-k selected by a multiplexer 63 are energized with a transmitting pulses which are supplied from a transmitting circuit 64 via delay lines or phase shifters 65-1 to 65-k. The delay times of the delay lines 65-1 to 65-k are so determined that the acoustic surface wave pulses are focused at a point 67. Then the acoustic surface wave of a fan-shape is considered to be projected from the point 67. The acoustic surface wave is absorbed, while it propagates under the specimen 66. The wave is then received by electrodes 62-m to 62-n which are opposed to the electrodes 62-1 to 62-k from which the acoustic surface wave pulses have been transmitted. The transmitted signals thus obtained from the electrodes 62-m to 62-n are amplified and detected by an amplifier 68 and then are converted into digital signals by an analog-digital converter 69. The digital signals thus derived are temporarily stored in a magnetic disc 70 and are supplied to a computer 71. Then the above operation is repeated, while the transmitting electrodes and receiving electrodes are successively shifted such as 62-2 to 62-(k+1); 62-3 to 62-(k+2); . . . and 62-(m+1) to 62-(n+1); 62-(m+2) to 62-(n+2); . . . , respectively, while the delay times of the delay lines 65-1 to 65-k are remained constant. If the data obtained after the scanning of one turn is not enough to produce an image, the focal point 67 is moved in a radial direction by a small amount shorter than the resolution by changing the delay times of the delay lines 65-1 to 65-k and the above operation is carried out. The successive steps explained above are repeated until a solution derived from the computer 71 is converted in accordance with the reproduction algorism. The image signal reproduced by the computer 71 is once stored in the magnetic disc 70 and then is converted into an analog image signal by a digital-analog converter 72. The analog image signal thus obtained is displayed on a television monitor 73. Also in this embodiment, the piezo-electric body 61 is surrounded by a frame 63 made of acoustic wave absorbing material.

The present invention is not limited to the embodiments explained above, but may be modified in various ways. For instance, in FIG. 3 the acoustic surface wave electrodes may be arranged circularly, in FIG. 4 the electrodes may be aligned linearly and in FIG. 5 the electrodes may be arranged into two arrays opposed to each other. Further, the corelation treatment may be equally applied to the embodiments shown in FIGS. 3 and 5. Moreover, a tomographic image of the specimen may be obtained by receiving both the reflected and transmitted acoustic surface waves.

As explained above in detail, according to the invention since the signal detecting unit including the acoustic surface wave electrodes and the acoustic surface wave propagating medium can be made simple and small, it can be easily installed in a distal end of the endoscope such as the gastroscope and hysteroscope. Moreover, the acoustic microscope device according to the invention may be advantageously used during surgical operations. Since the acoustic surface wave has the lower velocity than the longitudinal acoustic wave which has been used in the known acoustic microscope, it is possible to attain the higher resolution. In the acoustic surface wave, the frequency and range are determined exclusively by the shape of the acoustic surface wave electrodes and therefore, it is easy to obtain the higher frequency and wider range. When the acoustic surface wave electrodes are constructed in the same shape as the matching filter, the resolution can be further increased by means of the frequency composition. Moreover, in the propagation of the acoustic surface wave, it is sufficient to consider the two-dimensional space frequency and thus, the known technique for the aperture composition and computed tomography can be utilized as it is, so that the higher resolution can be attained.

What is claimed is:

1. An acoustic microscope device for producing an image of a specimen to be inspected comprising:
an acoustic surface wave propagating medium for contacting a specimen;
a plurality of electrodes arranged along a straight line on said medium with a given pitch and constructed to generate an acoustic surface wave along a surface of the medium;
circuit means connected to said electrodes for coupling a least selected ones of said electrodes such that acoustic surface waves are radiated from said selected electrodes along the surface of the medium to scan a specimen so that the acoustic surface waves are modulated in accordance with the difference in acoustic impedance between the specimen and medium thereby causing reflected acoustic surface waves which are received by said electrodes; and
a plurality of phase difference providing means coupled to said circuit means for causing the acoustic surface waves generated by said selected electrodes to have phase differences such that the acoustic surface waves are focussed at a focal point on said medium, said circuit means and phase difference providing means being further constructed and arranged to select the position and number of electrodes and vary the phase differences such that the focal point is moved two-dimensionally over the surface of the medium so that the reflected acoustic surface waves received by said selected electrodes enable the formation of a tomographic image of the specimen adjacent a surface of the specimen in contact with said medium.

2. An acoustic microscope device for producing an image of a specimen to be inspected comprising:
an acoustic surface wave propagating medium for contacting a specimen;
a plurality of electrodes arranged in a ring shaped configuration on said medium with a given pitch and constructed to generate an acoustic surface wave along a surface of the medium;
circuit means connected to said electrodes for coupling a least selected ones of said electrodes such that acoustic surface waves are radiated from said selected electrodes along the surface of the medium to scan a specimen so that the acoustic surface waves are modulated in accordance with the difference in acoustic impedance between the specimen and medium thereby causing reflected acoustic surface waves which are received by said electrodes; and a plurality of phase difference providing means coupled to said circuit means for causing the acoustic surface waves generated by said selected electrodes to have phase differences such that the acoustic surface waves are focussed at a focal point on said medium.

3. An acoustic microscope device for producing an image of a specimen to be inspected comprising:

an acoustic surface wave propagating medium for contacting a specimen;

a plurality of electrodes arranged in a ring shaped configuration on said medium with a given pitch and constructed to generate an acoustic surface wave along a surface of the medium;

circuit means connected to said electrodes for coupling a least selected ones of said electrodes such that acoustic surface waves are radiated from said selected electrodes along the surface of the medium to scan a specimen so that the acoustic surface waves are modulated in accordance with the difference in acoustic impedance between the specimen and medium thereby causing reflected acoustic surface waves which are received by said electrodes; and a plurality of phase difference providing means coupled to said circuit means for causing the acoustic surface waves generated by said selected electrodes to have phase differences such that the acoustic surface waves are focussed at a focal point on said medium, said circuit means and phase difference providing means being further constructed and arranged to select the position and number of electrodes and vary the phase differences such that the focal point is moved two-dimensionally over the surface of the medium so that the reflected acoustic surface waves received by said selected electrodes enable the formation of a tomographic image of the specimen adjacent a surface of the specimen in contact with said medium.

4. An acoustic microscope device according to claim 3, wherein the acoustic surface waves which have propagated under specimen are received by the selected electrodes which are opposed to those from which the acoustic surface waves have been generated so that a tomographic image of the specimen near its surface which is in contact with the medium is obtained by processing electric signals from the opposed electrodes in accordance with a given algorithm.

5. An acoustic microscope device according to claim 4, wherein the position of the electrodes from which the acoustic surface waves are to be generated is successively shifted by one turn, while the phase differences are unchanged.

6. An acoustic microscope device according to claim 4, 1, 3 or 2, wherein said phase differences are so changed that the acoustic surface waves are projected from different directions, while the focal point is maintained stationary, and a corelation of electric signals supplied from the electrodes which receive the modulated acoustic surface waves is derived to obtain the image information at the relevant focal point.

7. An acoustic microscope device comprising;

an acoustic surface wave propagating medium;

a plurality of electrodes disposed on said medium; and means for causing selected ones of said plurality of electrodes to generate acoustic surface waves in such a manner that the acoustic surface waves are focussed at a focal point on said medium and said focal point is moved two-dimensionally on said medium.

8. An acoustic microscope system comprising;

an acoustic surface wave propagating medium;

a specimen having a surface in contact with said medium;

a plurality of electrodes disposed on said medium;

means for causing selected ones of said plurality of electrodes to generate acoustic surface waves along a surface of said medium in contact with the surface of said specimen such that said acoustic surface waves scan said specimen and produce reflected surface waves received by said selected electrodes; and means for detecting said reflected acoustic surface waves to create an image of said specimen.

9. An acoustic microscope system comprising;

an acoustic surface wave propagating medium;

a specimen having a surface in contact with said medium;

a plurality of electrodes disposed on said medium;

means for causing selected ones of said plurality of electrodes to generate acoustic surface waves along a surface of said medium in contact with the surface of said specimen such that said acoustic surface waves scan said specimen and produce reflected surface waves received by said selected electrodes;

means for causing said selected ones of said plurality of electrodes to generate acoustic surface waves in such a manner that the acoustic surface waves are focussed at a focal point on said medium and said focal point is moved two-dimensionally on said medium; and means for detecting said reflected acoustic surface waves to create an image of said specimen.

* * * * *